(12) United States Patent
Beausoleil

(10) Patent No.: US 7,307,732 B2
(45) Date of Patent: Dec. 11, 2007

(54) PHOTONIC CRYSTAL INTERFEROMETER

(75) Inventor: Raymond G. Beausoleil, Redmond, WA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 281 days.

(21) Appl. No.: 11/141,286

(22) Filed: May 31, 2005

(65) Prior Publication Data

US 2006/0066867 A1 Mar. 30, 2006

Related U.S. Application Data

(63) Continuation-in-part of application No. 10/951,916, filed on Sep. 27, 2004.

(51) Int. Cl.
*G01B 9/02* (2006.01)

(52) U.S. Cl. .................................................. 356/477

(58) Field of Classification Search ............... 356/477; 385/12, 14, 1–10, 16–27, 37; 250/227.27
See application file for complete search history.

(56) References Cited

U.S. PATENT DOCUMENTS

| | | | | |
|---|---|---|---|---|
| 2,568,589 | A * | 9/1951 | Labhart | 356/517 |
| 5,396,328 | A * | 3/1995 | Jestel et al. | 356/482 |
| 6,330,064 | B1 * | 12/2001 | Rieder | 356/481 |
| 6,493,090 | B1 * | 12/2002 | Lading et al. | 356/484 |
| 6,917,431 | B2 * | 7/2005 | Soljacic et al. | 356/477 |
| 2002/0048422 | A1 * | 4/2002 | Cotteverte et al. | 385/4 |
| 2002/0115002 | A1 * | 8/2002 | Bailey et al. | 430/5 |
| 2003/0011775 | A1 * | 1/2003 | Soljacic et al. | 356/450 |
| 2004/0081384 | A1 * | 4/2004 | Datesman et al. | 385/12 |
| 2005/0128581 | A1 * | 6/2005 | Samuels et al. | 359/443 |

OTHER PUBLICATIONS

Jones, C.R. et al., "Two-beam Interferometer for Optical Constants Measurements at Near-millimeter Wavelengths", International Journal of Infrared and Millimeter Waves, vol. 5, No. 3, (1984), pp. 291-292.*
Topol'ancik, J. et al., "Fluid detection with photonic crystal-based multichannel waveguides", Applied Physics Letters, vol. 82 (Feb. 23, 2003), pp. 1143-1145.*
Luff, J., "Integrated Optical Mach-Zehnder Biosensor", Journal of Lightwave Technology, vol. 16, (Apr. 1998), pp. 583-592.*
Harrison, D.M., "Mach-Zehnder Interferometer", (Mar. 16, 1999), Available at: http://web.archive.org/web/20030218090055/http://www.upscale.utoronto.ca/GeneralInterest/Harrison/MachZehnder/MachZehnder.html.*
E A Camargo et al-"Mach-Zehnder Channel-Guide Device Structure Based on 2D Photonic Crystal"-Proc of the SPIE vol. 5450 No. 1—Apr. 29, 2004—pp. 333-343.
B J Luff et al-"Integrated Optical Mach-Zehnder Biosensor"-Journal of Lightwave Technology vol. 16 No. 4—Apr. 1998.
Ancik J Topol-"Fluid Detection With Photonic Crystal-Based Multichannel Waveguides"-Applied Physics Letters—vol. 82 No. 8-Feb. 24, 2003-pp. 1143-1145.

* cited by examiner

*Primary Examiner*—Michael P. Stafira

(57) ABSTRACT

A sensor apparatus comprising a photonic crystal structure optically coupled to a laser, the photonic crystal structure comprising a beam splitter, an interferometer having a reference arm and a sensor arm, a first output configured to be optically coupled to a bright port photodetector, and a second output configured to be optically coupled to a dark port photodetector.

17 Claims, 5 Drawing Sheets

PHOTONIC CRYSTAL INTERFEROMETER

RELATED APPLICATIONS

This application is a continuation-in-part of U.S. patent application Ser. No. 10/951,916 filed on Sep. 27, 2004 entitled "Photonic Crystal Laser Sensor and Methods," which is fully incorporated by reference herein.

FIELD OF THE INVENTION

This invention relates to sensor devices, and, more specifically, to interferometers using photonic crystal structures.

BACKGROUND

Michelson interferometers are instruments used to obtain optical measurements. Interferometers have been incorporated into spectroscopic based systems that have proved to be effective in many types of chemical detection devices. For example, chemical detection devices used for detecting the presence of gasses in air use light spectrums to detect the presence or absence of various chemicals. A device might pass a sample of air through a filter that has a surface coating configured to trap or adhere to various chemical vapors. The trapped molecules are burned or vaporized to produce an electromagnetic spectrum, for example, a light spectrum. Analyzing the light spectrum produced allows the presence (or absence) of a chemical to be determined. The spectrometer is used to split the various wavelength components of the light spectrum and produce a pattern of lines which are indicative of the presence or absence of a chemical. Mass spectroscopic-based systems such as these are typically too large and require too much power to be portable.

Other types of chemical detection devices use quartz crystals as mechanical oscillators. The frequency of an oscillating quartz crystal is monitored to detect a change that would result from absorption of molecules of a particular chemical. The change in frequency is measured to detect the presence of the chemical. The change in mass, however, of quartz crystal oscillators as chemical vapors are absorbed can be very small, resulting in a change in the frequency of oscillation that is also very small. This limits the sensitivity of this type of quartz crystal-based detection device, which in turn reduces the number of applications that can reliably employ such a device.

There is a need for a sensing device that overcomes these shortcomings.

SUMMARY

An embodiment of the present invention teaches a highly sensitive, compact, power efficient sensing device that uses a laser optically coupled to a photonic crystal structure. The exemplary device uses evanescent fields the sensing process.

In one exemplary embodiment, the invention is a sensor apparatus comprising a photonic crystal structure optically coupled to a laser. The photonic crystal structure comprises a beam splitter, an interferometer having a reference arm and a sensor arm, a first output configured to be optically coupled to a bright port photodetector, and a second output configured to be optically coupled to a dark port photodetector.

BRIEF DESCRIPTION OF THE DRAWINGS

For the purpose of illustrating the invention, there is shown in the drawings one exemplary implementation; however, it is understood that this invention is not limited to the precise arrangements and instrumentalities shown.

DETAILED DESCRIPTION

Overview

Evanescent fields are created as a result of the phenomena of total internal reflection of light. An evanescent field is an exponentially decaying field which is created on the opposite side of a totally internally reflecting interface. Evanescent fields are commonly associated with photonic crystal structures. Such fields can be used to allow for sensors and sensing methods in accordance with exemplary embodiments of the present invention.

Figure 1:
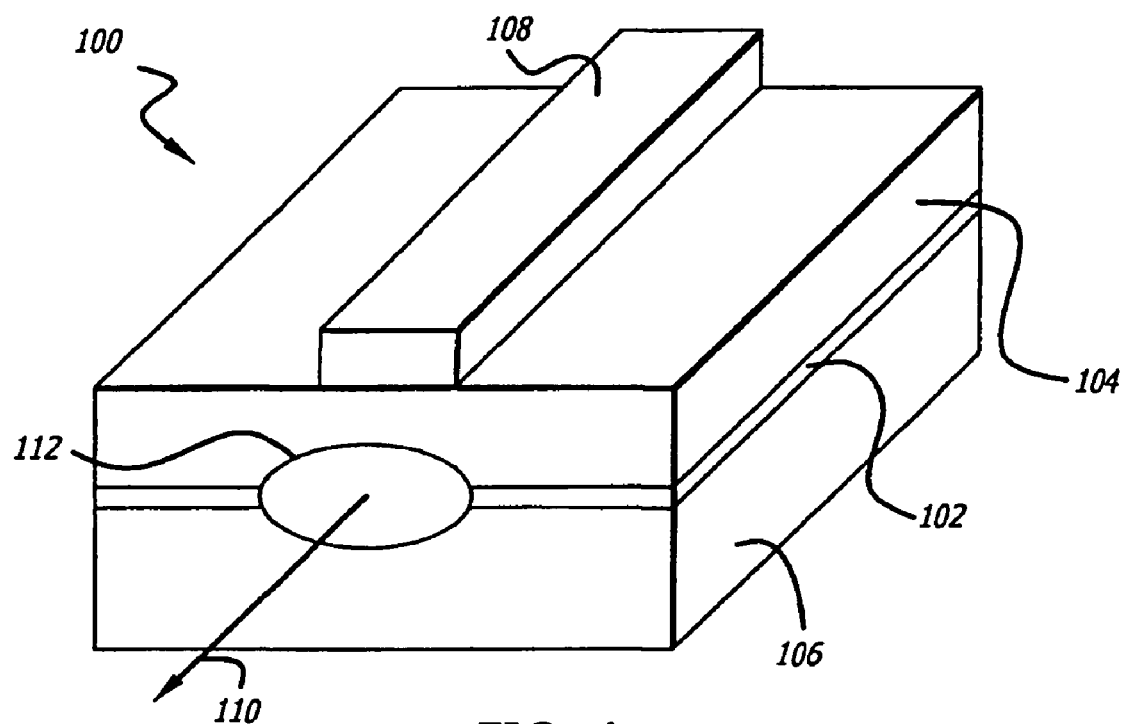
FIG. 1 illustrates an exemplary ridge semiconductor laser.
Figure 2:
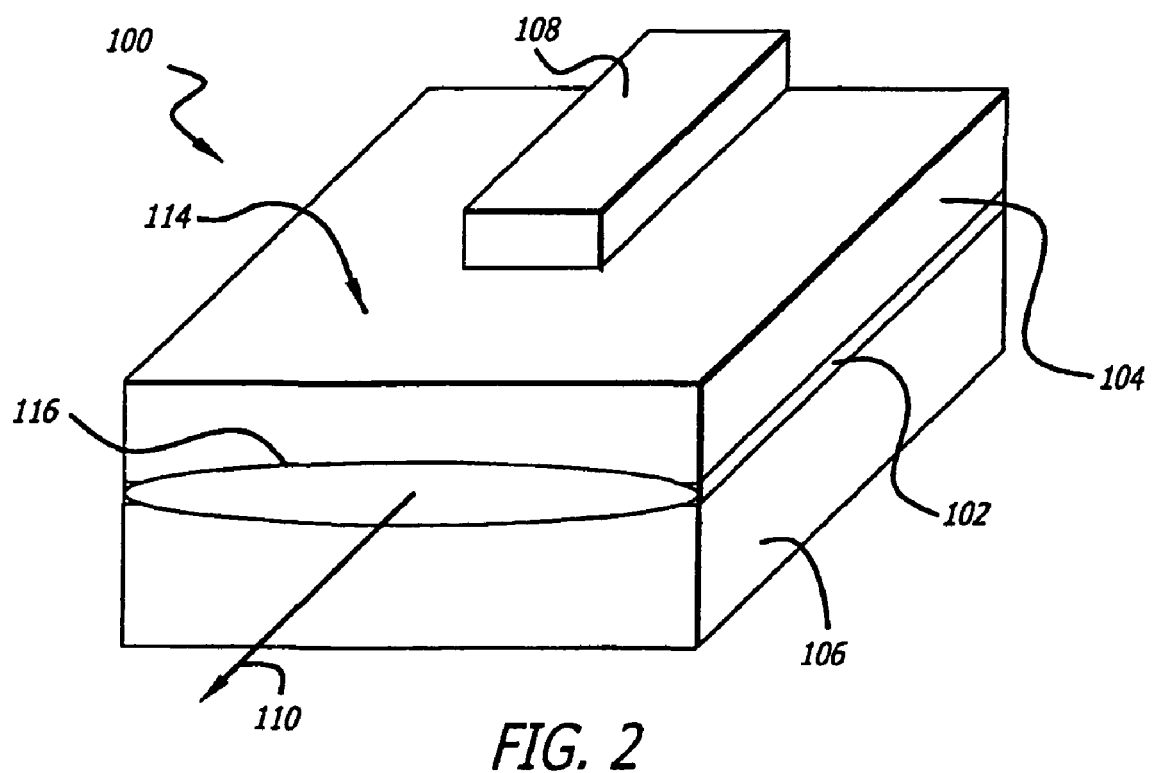
FIG. 2 illustrates the laser of FIG. 1 with the partial removal of the ridge such that light is no longer being confined under the ridge and goes into a slab mode.

Referring to FIG. 1, an exemplary ridge semiconductor laser 100 is shown. The laser 100 includes an active layer 102, an overclad layer 104, an underclad layer 106, and a ridge 108. Light output (along a direction denoted by arrow 110) from the ridge semiconductor laser 100 is guided by the ridge 108 as indicated by ellipse 112. Referring to FIG. 2, the ridge semiconductor laser 100 may be modified to partially remove the ridge 108 in region 114 such that the light is no longer confined under the ridge 108. The light pattern formed is elliptical in nature, and is represented by ellipse 116.

Figure 3:
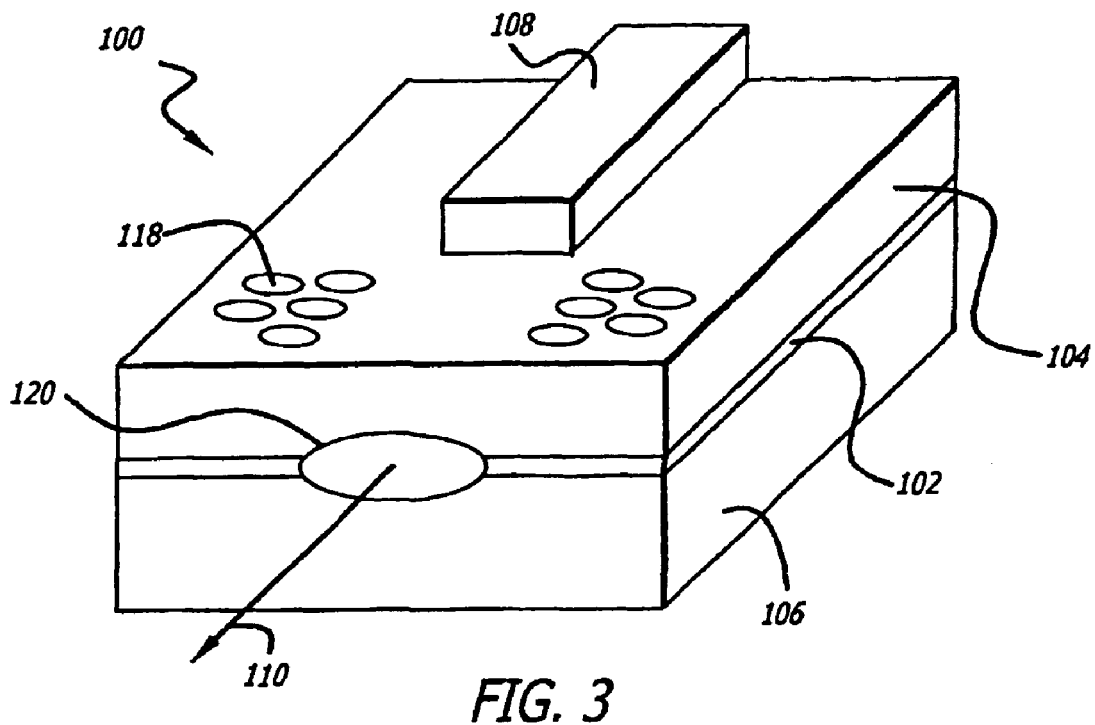
FIG. 3 illustrates the formation of photonic crystal voids on the semiconductor laser surface of FIG. 2 to guide the light.

Referring next to FIG. 3, photonic crystal voids 118 may be formed on the semiconductor laser surface. These voids act to modify the light pattern as indicated by ellipse 120. The result is a photonic crystal laser structure. In the illustrated embodiment, the overclad layer 104 and the underclad layer 106 have refractive indices lower than that of the core layer 102. All three layers are patterned with the photonic crystal structure, which is used to define a waveguide. An optical signal traveling in the waveguide is confined in the horizontal direction (i.e., the direction of arrow 110) by the photonic crystal structure, and in the vertical direction by the lower refractive index cladding layers.

Figure 4A:
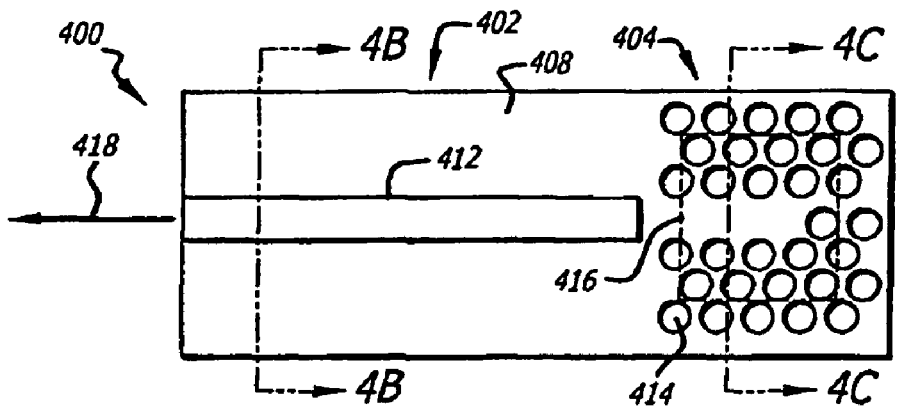
FIG. 4A is a top view of a laser sensor apparatus with a photonic crystal mirror in accordance with an embodiment of the present invention.
Figure 4B:
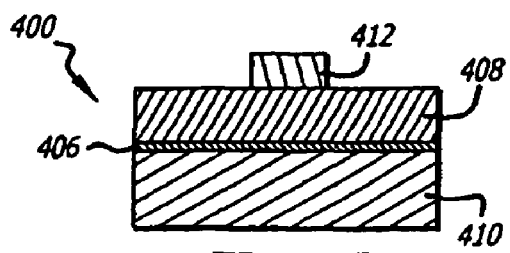
FIGS. 4B and 4C are cross-sectional views of the laser sensor apparatus with a photonic crystal mirror of FIG. 4A in accordance with an embodiment of the present invention.
Figure 4C:
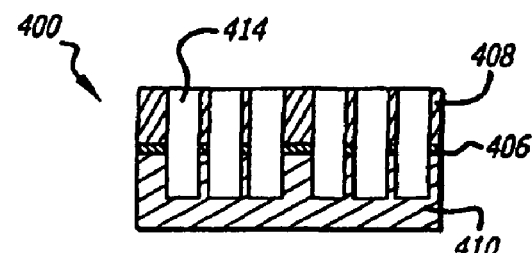

Photonic crystal structures can be used to provide an evanescent field through a sensed medium region such that the photonic crystal structure functions as a cavity resonator for the laser. Referring to FIGS. 4A-4C, a laser sensor apparatus 400 includes a laser 402 and a photonic crystal mirror structure 404 which is optically coupled to the laser 402 as shown. In this example, the laser 402 is a semiconductor laser that includes an active layer 406, an overclad layer 408, an underclad layer 410, and a ridge 412; however, it should be appreciated that the principles described herein are applicable to other light sources (e.g., fiber lasers). The photonic crystal mirror structure 404 in this embodiment includes photonic crystal voids 414 formed in a pattern as shown through the overclad layer 408, the active layer 406, and the underclad layer 410. The photonic crystal mirror structure 404 is also provided with a sensed medium region 416 (shown in dashed lines) positioned over the photonic crystal waveguide defined by the voids 414. In operation, a chemical, biological or other medium (e.g., cyanide or anthrax) is placed in the sensed medium region 416. The evanescent field resulting from light propagating along the photonic crystal structure can probe the medium. More specifically, an evanescent tail of the mode propagating along the photonic crystal waveguide structure passes through the medium, and the resulting interactions with the medium can alter the propagation speed and/or attenuation of the evanescent tail. The thickness of the overclad layer 408 can also be adjusted to provide a receptacle for the medium, to accommodate the refractive indices of various combinations of core and cladding materials, etc. In this embodiment, the voids 414 are arranged in a pattern that provides the photonic crystal mirror structure 404. Thus, interaction between the evanescent field and the medium in the sensed medium region 416 effects the characteristics of the light (denoted by arrow 418) reflected by the photonic crystal mirror structure 404, thereby providing an output indicative of the sensed medium.

With respect to materials, the photonic crystal structures (e.g., nanostructures and sub-micron structures) can be fabricated on III-V semiconductor materials (e.g., GaAs or InP and their alloys). Molecular beam epitaxy (MBE) can be used to fabricate very thin layers for the II-V semiconductors with very accurate control during epitaxial growth.

Other materials can be used to fabricate the planar photonic crystal waveguides described herein. Generally, the bulk materials can be any material substantially transparent to the wavelengths of the optical signal. For example, the planar photonic crystal bulk material can be doped silica, undoped silica, silicon, a polymeric organic material, an organic/inorganic hybrid material, an inorganic glass (e.g., chalcogenide glass), or any other suitable materials. The difference in refractive index between the core and the cladding layers can be achieved by using two substantially different materials, or by selectively doping similar materials, or by other methods known to those skilled in the art. The voids can be filled with air, or with another material (e.g., glass or water). In various embodiments, the material of the voids has a refractive index that is substantially different than the bulk photonic crystal material. The geometry of the pattern of voids (more generally, the "photonic crystal structures") can be hexagonal, square, triangular, rectangular, or otherwise, depending on the in-plane photonic band gap desired. Moreover, the voids can be formed with shapes other than cylindrical (e.g., ellipsoidal, rectangular, or rhomboidal).

The photonic crystal structures described herein can be fabricated in a variety of different ways. Nanoimprinting, a technique using nanoscale to sub micron and micron scale patterns to stamp or print designs on chip surfaces, can be used. By way of example, a nanoimprinting technique can involve using a hard mold to create nanoscale features by directly imprinting into a polymer film. After a pattern has been imprinted, the photonic crystal defects are created by etching the pattern (e.g., anisotropic dry etching with reactive ions).

Other photonic crystal structure fabrication techniques can be employed. For example, a focused ion beam (FIB) can be used to drill the photonic crystal holes. To address any damage to optical/electrical quality caused by FIB, additional optical pumping and/or electrical charge can be provided on the photonic crystal part to recover losses. Ultraviolet (UV) laser lithography, laser interference lithography, and electron-beam lithography can also be used.

Figure 5:
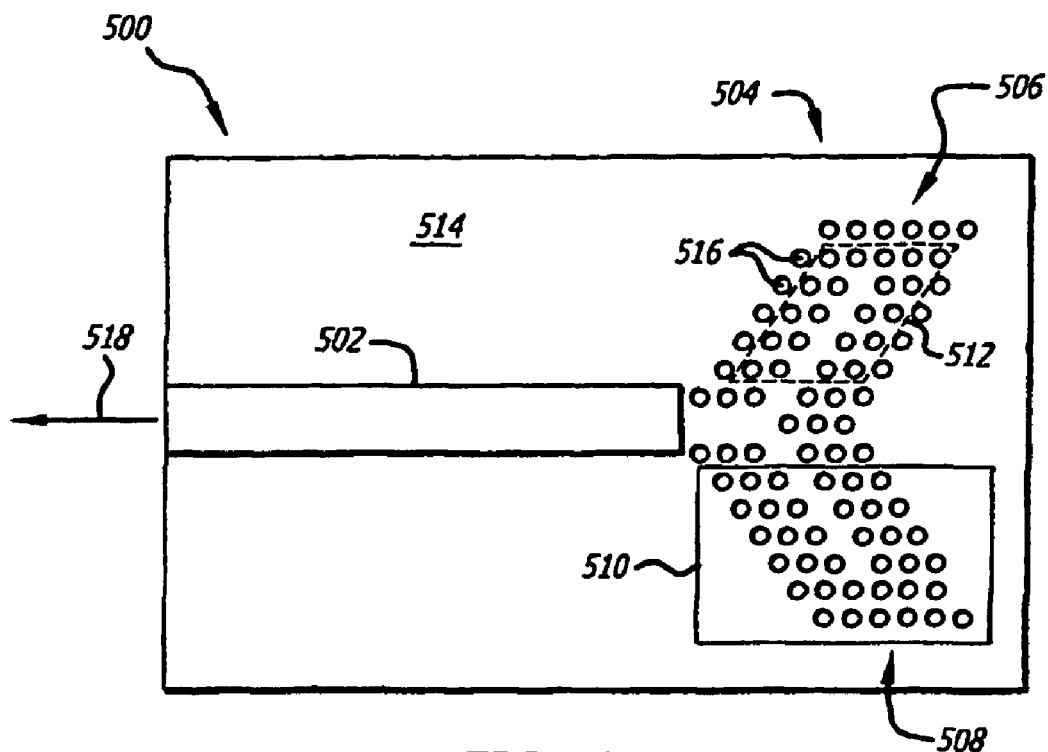
FIG. 5 is a top view of a laser sensor apparatus with a photonic crystal double pass interferometer that includes a sensor arm and a passivated reference arm in accordance with an embodiment of the present invention.

Photonic crystal mirrors can be used in an interferometric arrangement in a sensor apparatus. Referring to FIG. 5, an exemplary laser sensor apparatus 500 includes a laser 502 (e.g., a semiconductor laser) and a photonic crystal double pass interferometer structure 504 which is optically coupled to the laser 502 as shown. In this example, the photonic crystal double pass interferometer structure 504 includes a sensor arm 506 and a reference arm 508 in a Y-configuration as shown. At the end of each arm, a photonic crystal mirror is provided. In this example, the reference arm 508 is passivated, as indicated by passivation region 510. The photonic crystal double pass interferometer structure 504 is also provided with a sensed medium region 512 (shown in dashed lines) positioned over the photonic crystal waveguide of the sensor arm 506. In operation, a chemical, biological or other medium is placed in the sensed medium region 512. The evanescent field resulting from light propagating along the photonic crystal structure can probe the medium. More specifically, the evanescent tail of the mode propagating along the photonic crystal waveguide structure passes through the medium, and the resulting interactions with the medium can alter the propagation speed and/or attenuation of the evanescent tail. In this example, the thickness of the overclad layer 514 (of the laser 502) can also be adjusted to provide a receptacle for the medium, to accommodate the refractive indices of various combinations of core and cladding materials. In this embodiment, voids 516 are arranged in a pattern that provides the photonic crystal double pass interferometer structure 504. Thus, interaction between the evanescent field and the medium in the sensed medium region 512 effects the characteristics of the light (denoted by arrow 518) reflected by the photonic crystal double pass interferometer structure 504, thereby providing an output indicative of the sensed medium.

Figure 6:
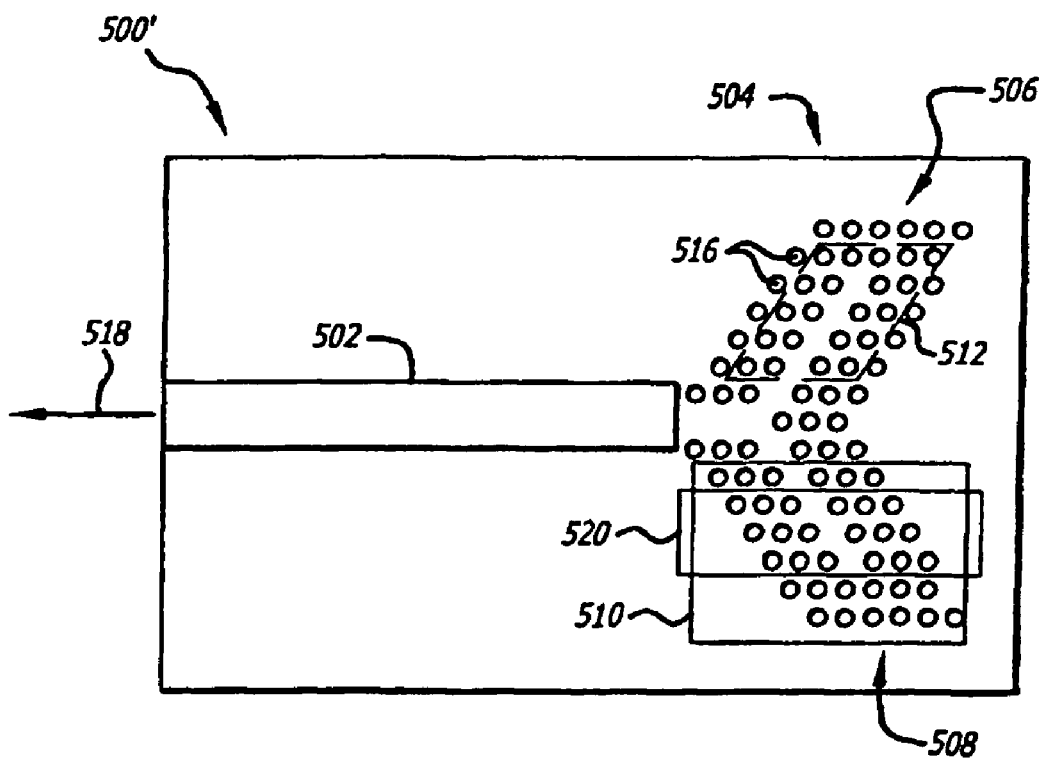
FIG. 6 is a top view of the laser sensor apparatus with a photonic crystal double pass interferometer of FIG. 5 provided with a phase shifter.

Referring to FIG. 6, in another embodiment, the reference arm 508 of an otherwise identical laser sensor apparatus 500' is provided with a phase shifter 520 for adjusting the operating point of the laser at an optimal or desired sensitivity point for detection (e.g., of a particular type or species of medium). The phase shifter 520 can also be used for biasing out manufacturing defects, compensating for contamination, and resetting the laser sensor apparatus 500' to a new operating point.

Figure 7:
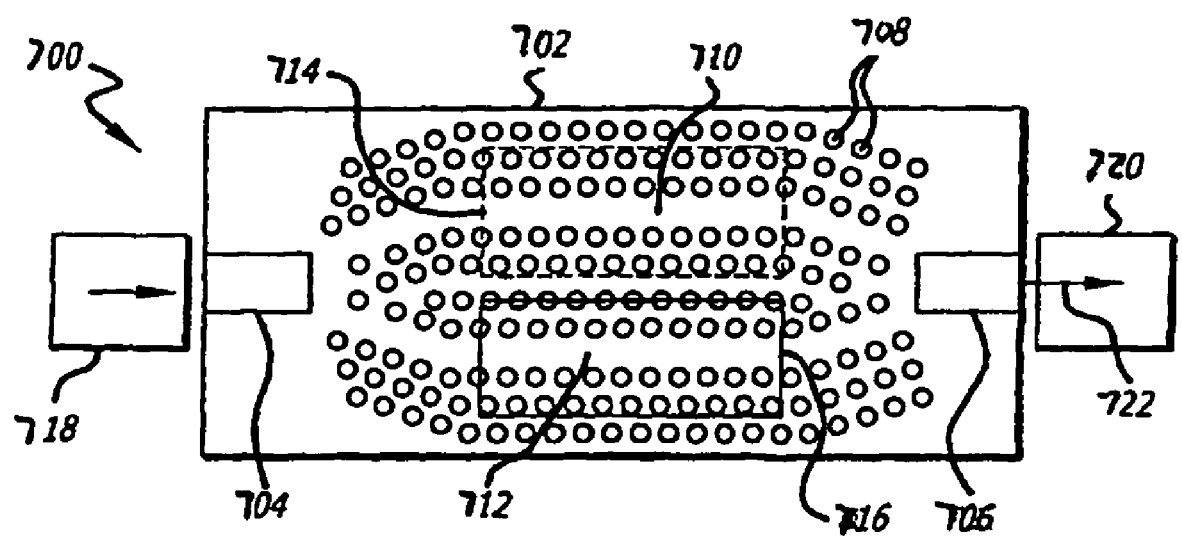
FIG. 7 is a top view of a Mach-Zehnder planar photonic crystal waveguide sensor in accordance with an embodiment of the present invention.

Additionally, the photonic crystal structures as described herein can be used to provide passive sensor apparatuses such as a Mach-Zehnder interferometer. Referring to FIG. 7, a Mach-Zehnder planar photonic crystal waveguide sensor 700 includes a photonic crystal Mach-Zehnder interferometer structure 702 and conventional waveguide-to-photonic crystal transition elements 704 and 706 which are optically coupled as shown to the input and the output of the photonic crystal Mach-Zehnder interferometer structure 702, respectively. In this embodiment, the photonic crystal Mach-Zehnder interferometer structure 702 includes voids 708 arranged in one possible pattern defining a sensor waveguide arm 710 and a reference waveguide arm 712 as shown.

Other dual arm patterns may also be used. The photonic crystal Mach-Zehnder interferometer structure 702 is also provided with a sensed medium region 714 (shown in dashed lines) positioned over the sensor waveguide arm 710. In this example, the reference waveguide arm 712 is provided with a phase shifter 716 for biasing out manufacturing defects, compensating for contamination, and resetting the Mach-Zehnder planar photonic crystal waveguide sensor 700 to a new operating point. Another method of phase shifting in addition to carrier injection either optically or electrically is to apply a DC bias and use the electro-optic effect in Ill-V semiconductors. A field is applied via a metal semiconductor or metal oxide semiconductor contact (not shown in FIG. 7) to the semiconducting region of the device. In this example, optical fibers 718 and 720 are optically coupled to the transition elements 704 and 706, respectively. In operation, a chemical, biological or other medium is placed in the sensed medium region 714. The evanescent field resulting from light propagating along the sensor waveguide arm 710 "probes" the medium. More specifically, the evanescent tail of the mode propagating along the sensor waveguide arm 710 passes through the medium, and the resulting interactions with the medium can alter the propagation speed and/or attenuation of the evanescent tail. By varying the optical path length of the sensor waveguide arm 710, the difference in optical path length between the sensor waveguide arm 710 and the reference waveguide arm 712 controls the interference of the optical signals propagating in those waveguides upon recombination. Thus, interaction between the evanescent field and the medium in the sensed medium region 714 affects the characteristics of the light (denoted by arrow 722) output by the photonic crystal Mach-Zehnder interferometer structure 702, thereby providing an output indicative of the sensed medium.

Modified Michelson Interferometer

Figure 8:
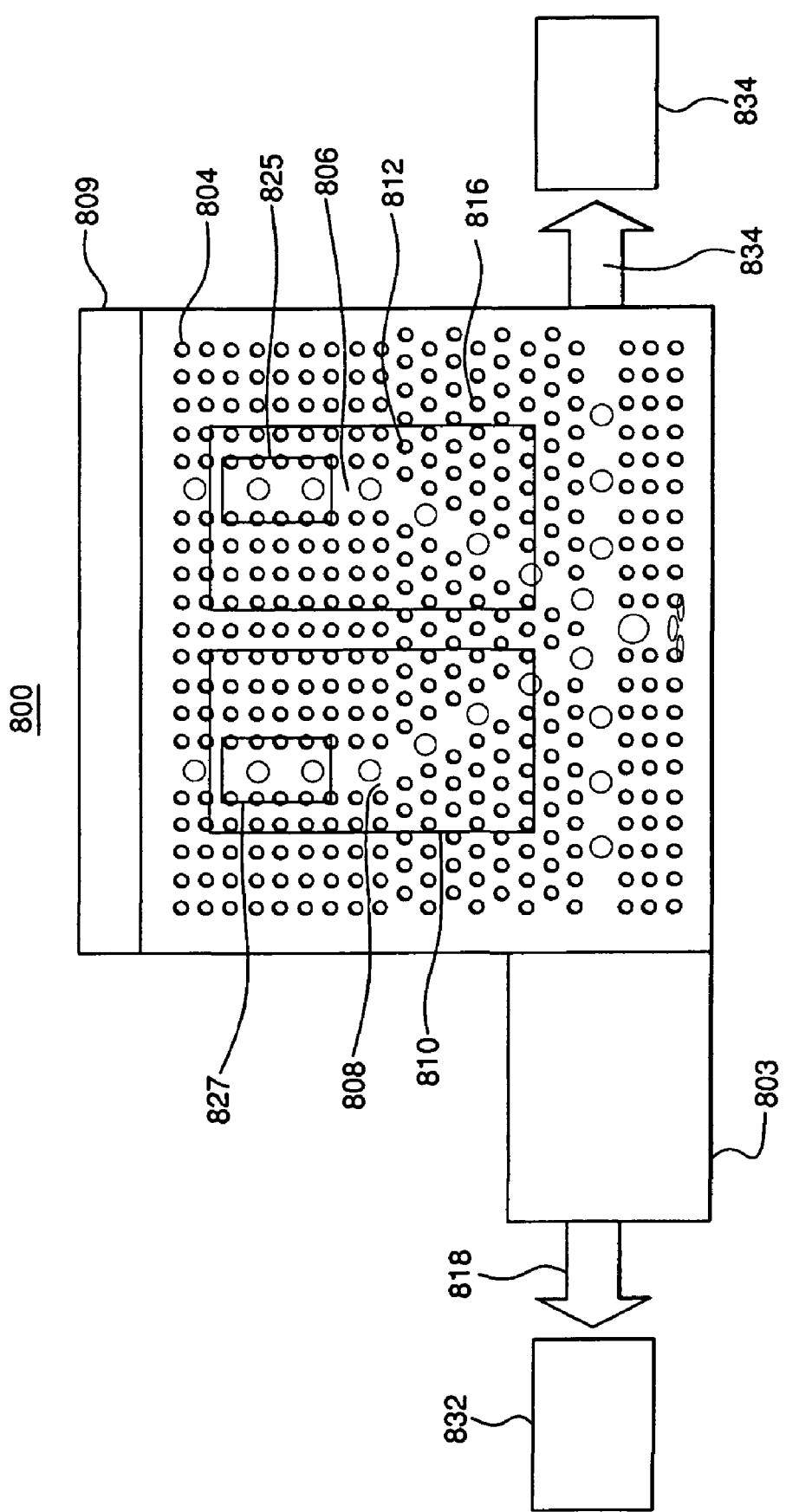
FIG. 8 is a top view of a Michelson planar photonic crystal waveguide sensor with a dark port output in accordance with an embodiment of the present invention.

Referring to FIG. 8, an embodiment of a Michelson interferometer device is shown that includes two output ports that allow the device to be less sensitive to the effects of frequency pulling and gain saturation. A laser sensor apparatus 800 includes a photonic crystal double pass interferometer structure 804 which is optically coupled to a semiconductor laser 803. The photonic crystal double pass interferometer structure 804 includes a sensor arm 806 and a reference arm 808. The illustrated embodiment shows the sensor arm 806 and the reference arm 808 positioned relative to each other to form a Y-configuration, although other configurations may also be used. At the end of each arm, a photonic crystal mirror 809 is provided (e.g., a Bragg mirror having a 100% reflectance). In one embodiment, the reference arm 808 is passivated, as indicated by passivation region 810.

Two output ports 832, 834 are included in the laser sensor apparatus 800. A light port 832 provides a first output from a semiconductor laser 803. The light port 832 is coupled to a photodetector (not shown) configured to receive a first optical output. Additionally, a dark port 834 provides a second output from the semiconductor laser 803. The dark port 834 is coupled to a photodetector (not shown) configured to receive a second optical output.

The photonic crystal double pass interferometer structure 804 has a sensed medium region 812 positioned over the photonic crystal waveguide of the sensor arm 806. In operation, a chemical, biological or other medium is placed in the sensed medium region 812. The evanescent field resulting from light propagating along the photonic crystal structure can probe the medium. More specifically, the evanescent tail of the mode propagating along the photonic crystal waveguide structure passes through the medium, and the resulting interactions with the medium can alter the propagation speed and/or attenuation of the evanescent tail. In this embodiment, voids 816 are arranged in a pattern that provides the photonic crystal double pass interferometer structure 804. Thus, interaction between the evanescent field and the medium in the sensed medium region 812 affects the characteristics of the light output (denoted by arrows 818) reflected by the photonic crystal double pass interferometer structure 804, thereby providing an output indicative of the sensed medium.

The output power from the laser output to the bright port 832 may be measured as an indication of the presence or absence of molecules in the sensed medium region 812. A decrease in output power observed at the bright port 832 is indicative of a portion of power being diverted to the dark port. By observing this decrease, identification of any absorption and/or any phase shift caused by the molecules in the sensed medium region is possible. However, the decrease caused by absorption is likely of such a small magnitude that it is difficult to observe. Additionally, the effects of frequency pulling within the laser will offset any decrease caused by absorption as the laser attempts to operate at a maximum gain. The effects caused by absorption and frequency pulling can be measured by observing the output from the dark port 834.

In the absence of any molecules in the sensed medium region, the light output 819 to the dark port 834 is set to zero. This is accomplished by tuning the DC phase shifter 827 to provide that any field that would be directed to the dark port 834 is cancelled when the sensed medium region does not contain any molecules. However, if molecules of a substance (e.g., the chemical that is the subject of the test) are present, it will cause an emission to emanate from the dark port as described below An AC phase-shifter 825 is added to the sensor arm 806. The AC phase shifter 825 is used to dither the phase within the sensor arm 806. This is done to compensate for any frequency pulling that may result from the presence of molecules in the sensed medium region 812.

The power P (e.g., as measured by a standard photodiode that measures the square of the electric field) emerging from the dark port of the Michelson interferometer is defined by the following equation:

$$P = |E|^2 \sin^2(\theta - \beta)$$

where E is the amplitude of the electric field in the sensor arm; $\theta$ is the AC phase shift applied by the phase shifter, and $\beta$ is the time-independent phase shift that arises from the presence of molecules captured in the sensor arm. If the angle $\theta$ is dithered as a function of time, the photocurrent can be differentiated as follows:

$$d\theta/dt \approx \sin^2[(\theta(t) - \beta]\theta(t)$$

Plotting dP/dt vs. d$\theta$/dt will yield $\theta(t) - \beta$. Taking the points where the curve crosses the x-axis (i.e., the zero points) will therefore yield $\beta$.

By determining the phase shift $\beta$ caused by absorption in the sensor region 812, it is possible to calibrate the device 800 to create desired steady state conditions. For example, in order to offset frequency pulse, a particular phase condition should be maintained. Similarly, in order to maximize the gain of the semiconductor laser 803, a different phase condition should be maintained. By calibrating the device in the desired steady state conditions, whereby the output to the dark port 834 is zero, and then monitoring the dark port 834 for any light emission, the presence of molecules in the sensed medium region 812 can be detected. It is possible to detect a low level of light emitting from the dark port 834 more accurately that it would have been possible to detect a slight variation in the light output to the bright port 832 because the steady state condition of the dark port 834 is a zero light output.

The device 800 in accordance with an embodiment of the present invention allows for the identification of phase conditions and thus calibration to create or maintain desired phase conditions. A variety of modifications to the embodiments described will be apparent to those skilled in the art from the disclosure provided herein. Thus, the present invention may be embodied in other specific forms without departing from the spirit or essential attributes thereof and, accordingly, reference should be made to the appended claims, rather than to the foregoing specification, as indicating the scope of the invention.

What is claimed is:

1. A sensor apparatus comprising:
   a photonic crystal structure optically coupled to a laser, said structure comprising:
   a beam splitter;
   an interferometer having a reference arm and a sensor arm, said reference arm and said sensor arm optically coupled to said beam splitter;
   a first output configured to be optically coupled to a bright port photodetector and said beam splitter;
   a second output configured to be optically coupled to a dark port photodetector and said beam splitter; and
   a photonic crystal mirror optically coupled to said photonic crystal structure, said photonic crystal mirror positioned to reflect light propagating in a first direction of said reference arm into a direction generally opposite said first direction in said reference arm and reflect light propagating in a second direction of said sensor arm into a direction generally opposite said second direction in said sensor arm.

2. The sensor apparatus as set forth in claim 1, wherein said interferometer is a double pass interferometer.

3. The sensor apparatus as set forth in claim 2, wherein said double pass interferometer comprises a Michelson interferometer.

4. The sensor apparatus as set forth in claim 1, wherein the presence of light at said second output indicates the presence of molecules in said sensor arm.

5. The sensor apparatus as set forth in claim 1, further comprising a DC phase-shifter in said reference arm.

6. The sensor apparatus as set forth in claim 1, further comprising an AC phase-shifter in said sensor arm.

7. The sensor apparatus as set forth in claim 1, wherein said photonic crystal mirror comprises a photonic crystal Bragg mirror.

8. The sensor apparatus as set forth in claim 1, wherein said reference arm is passivated.

9. The sensor apparatus as set forth in claim 1, wherein said photonic crystal structure comprises III-V semiconductor materials.

10. The sensor apparatus as set forth in claim 1, wherein said photonic crystal structure comprises voids.

11. The sensor apparatus as set forth in claim 10, wherein said voids are formed by nanoimprinting a pattern.

12. A method for sensing comprising:
   providing a laser input to a photonic crystal structure having a sensed medium region;
   supplying an analyte in said sensed medium region;
   transmitting said laser input through said sensed medium;
   reflecting said laser input off of a photonic crystal mirror to transmit said laser input back through said sensed medium and into a first output and a second output of said photonic crystal structure; and
   detecting said analyte by measuring said first output and said second output of said photonic crystal structure.

13. The method as set forth in claim 12 wherein said first output and said second output comprise light.

14. The method of claim 13, wherein said first output emits from a bright port and said second output emits from a dark port.

15. The method of claim 14, wherein said bright port is configured to be coupled to a first photodetector and said dark port is configured to be coupled to a second photodetector.

16. A sensor apparatus comprising:
   means for generating a laser input to a photonic crystal structure having a sensed medium region containing an analyte;
   means for transmitting said laser input through said sensed mediurm
   means for reflecting said laser input back through said sensed medium region into a first output and a second output of said photonic crystal structure; and
   means for detecting said analyte by measuring said first output and said second output of said photonic crystal structure.

17. The sensor apparatus as set forth in claim 16 wherein said detecting means further comprise a bright port configured to be coupled to a first photodetector and a dark port configured to be coupled to a second photodetector for measuring said first and second outputs of said photonic crystal structure.

* * * * *

UNITED STATES PATENT AND TRADEMARK OFFICE
CERTIFICATE OF CORRECTION

PATENT NO. : 7,307,732 B2  Page 1 of 1
APPLICATION NO. : 11/141286
DATED : December 11, 2007
INVENTOR(S) : Raymond G. Beausoleil It is certified that error appears in the above-identified patent and that said Letters Patent is hereby corrected as shown below:

In column 3, line 37, delete "II-V" and insert -- III-V --, therefor.

In column 5, line 24, delete "andlor" and insert -- and/or --, therefor.

In column 8, line 39, in Claim 16, delete "mediurm" and insert -- medium; --, therefor.

Signed and Sealed this

Fourteenth Day of July, 2009

JOHN DOLL
*Acting Director of the United States Patent and Trademark Office*